(12) United States Patent
Veith

(10) Patent No.: US 6,248,900 B1
(45) Date of Patent: Jun. 19, 2001

(54) PROCESS FOR PREPARING ALKOXYTRIAZOLINONES

(75) Inventor: Ulrich Veith, Visp (CH)

(73) Assignee: Lonza Group, Basel (CH)

( * ) Notice: Subject to any disclaimer, the term of this patent is extended or adjusted under 35 U.S.C. 154(b) by 0 days.

(21) Appl. No.: 09/509,525

(22) PCT Filed: Oct. 8, 1998

(86) PCT No.: PCT/EP98/06397

§ 371 Date: May 23, 2000

§ 102(e) Date: May 23, 2000

(87) PCT Pub. No.: WO99/18089

PCT Pub. Date: Apr. 15, 1999

(30) Foreign Application Priority Data

Aug. 10, 1997  (CH) ................................................ 2354/97

(51) Int. Cl.$^7$ .................................................. C07D 249/12
(52) U.S. Cl. ........................................................ 548/263.6
(58) Field of Search .......................................... 548/263.6

(56) References Cited

U.S. PATENT DOCUMENTS

| | | |
|---|---|---|
| 4,957,864 | 9/1990 | Takahashi . |
| 5,594,148 | 1/1997 | Wroblowsky et al. . |
| 5,599,945 | 2/1997 | Wroblowsky et al. . |
| 5,606,070 | 2/1997 | Wroblowsky et al. . |
| 5,708,183 | 1/1998 | Wroblowsky . |
| 5,710,303 | 1/1998 | Wroblowsky et al. . |
| 5,817,863 | 10/1998 | Wroblowsky . |

FOREIGN PATENT DOCUMENTS

| | | |
|---|---|---|
| 4433967 | 3/1996 | (DE) . |
| 0703224 | 9/1995 | (EP) . |
| 0703225 | 9/1995 | (EP) . |
| 0726258 | 1/1996 | (EP) . |

OTHER PUBLICATIONS

Mackay, D., et al., Canadian Journal of Chemistry, vol. 61, No. 6, (1983), pp 1213–1217.

Hantzsch, Chem. Ber., 1895, 29, 2470–2471.

Heydayatullah, M. Bull. Soc. Chem. Fr., 1967, 416.

*Primary Examiner*—Patricia L. Morris
(74) *Attorney, Agent, or Firm*—Fisher, Christen & Sabol

(57) ABSTRACT

A process for preparing alkoxytriazolinones of general formula (1):

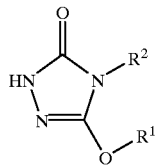

(I)

in which $R^1$ and $R^2$ independently represent an alkyl group, an aryl group, an arylalkyl group or cycloalkyl group. The alkoxytriazolinones are prepared by reacting, in a first stage, water-dissolved iminocarboxylic acid diesters in the presence of a mineral acid or by reacting a mixture of water with a water-miscible polar organic solvent and a carboxylic acid ester, yielding hydrazine carboxylic acid ester; and in a second stage, by further reacting the thus obtained reaction product with an amine, a polar organic solvent or mixtures thereof in the presence of water.

16 Claims, No Drawings

PROCESS FOR PREPARING ALKOXYTRIAZOLINONES

The present invention relates to a novel process for preparing alkoxytriazolinones of the general formula

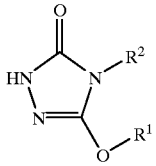

I and a novel hydrazinecarboxylic acid ester of the general formula

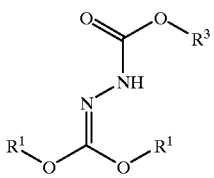

IV which serves as intermediate in the preparation according to the invention of the alkoxytriazolinones. Alkoxytriazolinones are important intermediates for preparing agrochemically active compounds.

$R^1$, $R^2$ and $R^3$ independently of one another are an optionally substituted straight-chain or branched $C_{1-6}$-alkyl group. Methyl, ethyl, propyl, isopropyl, butyl, isobutyl, tert-butyl, pentyl and its isomers and hexyl and its isomers may be mentioned by name.
Moreover, $R^1$ and $R^2$ independently of one another may be optionally substituted aryl, arylalkyl or cycloalkyl. Aryl has preferably the meaning phenyl. Arylalkyl is preferably phenylalkyl, for example phenyl-$C_{1-6}$-alkyl, and particularly preferably benzyl. Cycloalkyl is, in particular $C_{3-6}$-cycloalkyl, preferably cyclohexyl. Suitable substituents of the alkyl groups, the aromatic compounds of the aryl function, or the cycloalkyl groups are, for example, halogen, amino, alkylamino, dialkylamino, alkoxy or hydroxyl, where alkyl, as above, is preferably $C_{1-6}$-alkyl and alkoxy is preferably $C_{1-6}$-alkoxy. Here and below, halogen is to be understood as meaning fluorine, chlorine, bromine or iodine. $R^1$ is preferably methyl, propyl and phenyl, and particular preference is given to methyl and propyl. $R^2$ is preferably methyl, benzyl and cyclohexyl. $R^3$ is preferably methyl.

It was the object of the invention to provide an economical, industrially feasible process for preparing alkoxytriazolinones. This object is achieved by the process according to Patent claim 1 and by the novel intermediate according to Patent claim 10. According to the invention, in a first step, an iminocarbonic acid diester of the general formula

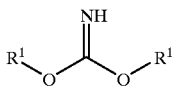

II in which $R^1$ has the abovementioned meaning, is reacted, in the presence of a mineral acid and dissolved in water or in a mixture of water with a water-miscible polar organic solvent, with a carbazinic acid ester of the general formula

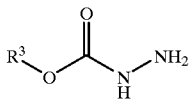

III in which $R^3$ has the meaning mentioned, to give a hydrazinecarboxylic acid ester of the general formula

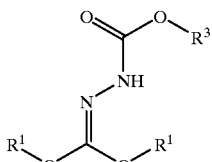

IV in which $R^1$ and $R^3$ have the meanings mentioned.

Iminocarbonic acid diesters of the general formula II can be prepared according to EP-A 0 523 619 or according to Hantzsch (Chem. Ber., 1895, 28, 2470–2471). Carbazinic acid esters are customary organic chemicals for synthesis.

The mineral acid used can be hydrochloric acid, phosphoric acid or sulphuric acid. Hydrochloric acid is particularly suitable.

Water-miscible polar organic solvents are expediently straight-chain or branched alcohols having 1 to 6 C atoms. Methanol, ethanol, propanol, isopropanol, butanol, isobutanol or tert-butanol, pentanol and its isomers and also hexanol and its isomers may be mentioned by name.

The reaction of the first step is expediently carried out at a temperature from −5 to 40° C., advantageously at from 0 to 20° C. The pH is expediently in a range from 3 to 10, advantageously in a range from 5 to 8.

After a customary reaction time of from 30 min to 2 hours, the compound of the general formula IV, which has hitherto not been described in the literature, can be isolated by customary methods, such as, for example, extraction, or be employed directly, without isolation, for the second step. The intermediate (formula IV) is preferably isolated.

In a second step, the hydrazinecarboxylic acid ester according to the invention (formula IV) is reacted with an amine of the general formula $R^2$—$NH_2$  V in which $R^2$ has the meaning mentioned, in the presence of water, a polar organic solvent or mixtures thereof, to give the end product of the formula I. The reaction is preferably carried out in the presence of a polar organic solvent.

The polar organic solvents used are expediently straight-chain or branched alcohols having 1 to 6 C atoms. Methanol, ethanol, propanol, isopropanol, butanol, isobutanol or tert-butanol, pentanol and its isomers and also hexanol and its isomers may be mentioned by name. Particular preference is given to methanol.

The reaction of the second step is expediently carried out at a temperature of from 10 to 200° C., advantageously from 20 to 100° C.

The reaction of the second step is expediently carried out via an intermediate of the general formula

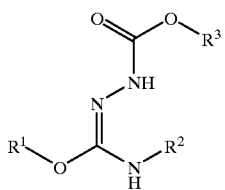

in which $R^1$, $R^2$ and $R^3$ have the meanings mentioned, which can, if appropriate, be isolated.

The reaction of the second step is expediently carried out using an excess of the amine of the general formula V, based on the hydrazinecarboxylic acid ester of the general formula IV. The amine of the general formula V is preferably employed in a ratio of 1.1:1 to 30:1, particularly preferably in a ratio of from 2:1 to 20:1, based on the hydrazinecarboxylic acid ester of the general formula IV.

Likewise expediently, the reaction of the second step can be carried out, after formation of the intermediate of the general formula VI, in the presence of a base. Suitable bases are alkali metal alkoxides, such as sodium methoxide or sodium ethoxide, and alkali metal hydroxides, such as sodium hydroxide or potassium hydroxide, in each case being optionally dissolved in the corresponding alcohol or in water.

After a customary reaction time of in total from 5 to 15 hours, the compound of the general formula I are obtained, and they can then be worked up by customary methods. Iminocarbonic acid diesters used as starting material for the preparation according to the invention of the alkoxytriazolinones can be prepared alternatively to the process as described in EP-A 0 523 619 and Hantzsch (Chem. Ber., 1895, 28, 2470–2471).

Here, an alcohol of the general formula $R^1$—OH <span style="float:right">VII</span> in which $R^1$ has the meaning mentioned is, in a first step, reacted with an alkali metal to give the corresponding alkoxide.

The alcohol used can be a straight-chain or branched alcohol having 1 to 6 C atoms. Methanol, ethanol, propanol, isopropanol, butanol, isobutanol, tert-butanol, pentanol and its isomers and also hexanol and its isomers may be mentioned by name. Preference is given to using methanol.

The alkali metal used can be sodium or potassium. Preference is given to using sodium.

The reaction of the first step is expediently carried out at a temperature of from 10 to 80° C., advantageously from 20 to 40° C.

In the second step, the alkoxide is reacted with a halocyanogen to give the end product of the formula II. The halocyanogen used is chlorocyanogen or bromocyanogen, preferably chlorocyanogen. The reaction of the second step is expediently carried out at a temperature from −20 to 20° C., advantageously at from −10 to 5° C.

After a customary reaction time of from 1 to 2 hours, the compound of the general formula II can be isolated or be employed directly, without isolation, as starting material for the preparation according to the invention of the alkoxytriazolinones.

The compound of the general formula II is preferably employed directly for the preparation according to the invention of the alkoxytriazolinones.

EXAMPLES

Example 1

Preparation of Methyl N'-dimethoxymethylenehydrazinecarboxylate 27.9 g (0.30 mol) of methyl carbazate were initially charged in water (50 ml) and, with cooling, admixed with 28.9 g (0.30 mol) of HCl (37.9% strength). At 0–7° C., a solution of 27.2 g (0.30 mol) of dimethyl iminocarbonate in water was added. The reaction mixture was then stirred for 1 hour and 40 minutes at 0° C. The reaction mixture was extracted with ethyl acetate and the organic phase was dried over magnesium sulphate and then concentrated under reduced pressure. This gave 37.9 g (77.8%) of methyl N'-dimethoxymethylenehydrazinecarboxylate in the form of a colourless solid which was recrystallized from toluene. Melting point 78.5–81.5° C.

| $^1$H-NMR (DMSO-d$^6$ 400 MHz): δ = | 3.55 (s, 3H); |
| --- | --- |
| | 3.73 (s, 3H); |
| | 3.74 (s, 3H); |
| | 8.86 (1H). |

Example 2

Preparation of Methyl N'-dimethoxymethylenehydrazinecarboxylate 10.6 g (0.263 mol) of NaOH (solid) were dissolved in methanol (61.1 g; 2.00 mol). The mixture was then cooled to 4° C. and the introduction of 15.5 g (0.25 mol) of chlorocyanogen was started. The introduction was continued for a total of 1 hour, and the suspension of dimethyl iminocarbonate was stirred at 5° C. for another hour (preparation of dimethyl iminocarbonate similar to the method of EP-A 0 523 619).

23.2 g (0.25 ml) of methyl carbazate were dissolved in water (100 ml). At 4–6° C., the resulting suspension of dimethyl iminocarbonate was added to this solution over a period of 30 min. By simultaneous addition of HCl (15% strength; 48.8 ml), the pH was kept constant at 7. After the addition had ended, stirring at 3° C. was continued for 1 hour, and the solution was concentrated under reduced pressure to 110 g. The reaction mixture was extracted with ethyl acetate and the organic phase was dried over magnesium sulphate and then concentrated under reduced pressure. This gave 25.3 g (52.9%; content 85%) of methyl N'-dimethoxymethylenehydrazinecarboxylate in the form of a colourless solid which was recrystallized from toluene. Melting point 78.5–81.5° C.

Example 3 a) Preparation of Dimethyl Iminocarbonate 64.1 g (2.00 mol) of methanol were admixed with 6.16 g (0.268 mol) of sodium metal. After all of the sodium had dissolved, the mixture was cooled to 3° C., and the introduction of 15.5 g (0.25 mol) of chlorocyanogen was started. The introduction was continued for a total of 1 hour and 15 minutes, and the suspension of dimethyl iminocarbonate was stirred at 0° C. for another hour.

b) Preparation of Methyl N'-dimethoxymethylenehydrazinecarboxylate 23.2 g (0.25 mol) of methyl carbazate were dissolved in water (100 ml). At 5–10° C., the suspension of dimethyl iminocarbonate obtained in Example 3a) was added to this solution over a period of 30 min. By simultaneous addition of HCl (15% strength; 52.1 ml), the pH was kept constant at 7. After the addition has ended, the mixture was stirred at 3° C. for another hour and 30 min and the solution was concentrated under reduced pressure to 110 g. The reaction mixture was extracted with ethyl acetate and the organic phase was dried over magnesium sulphate and then concentrated under reduced pressure. This gave 20.8 g (47.2%;

content 92%) of methyl N'-dimethoxymethylenehydrazinecarboxylate in the form of a colourless solid which was recrystallized from toluene. Melting point 78.5–81.5° C.

Example 4

Preparation of Methyl N'-dipropoxymethylenehydrazinecarboxylate 396.4 g (9.812 mol) of NaOH (solid) were dissolved in propanol (3600 g; 59.3 mol). The mixture was then cooled to from 0 to 5° C., and the introduction of 586.2 g (9.345 mol) of chlorocyanogen was started. The introduction was continued for a total of 3 hours, giving a pale yellow, fine suspension of dipropyl iminocarbonate.

772.1 g (8.4 mol) of methyl carbazate were dissolved in water (602 ml). At room temperature, the resulting suspension of dipropyl iminocarbonate was added to this solution over a period of 1 hour. By simultaneous addition of HCl (6% strength), the pH was kept constant at from 6.8 to 7. After the addition had ended, the apparatus was rinsed with propanol and water, and stirring was continued for 2 hours. The reaction mixture was extracted with ethyl acetate, recrystallized from hexane and subsequently dried under reduced pressure. This gave 1391 g (71.6%; content 94.4%) of methyl N'-dipropoxymethylenehydrazinecarboxylate in the form of a colourless solid. Melting point: 38.1–38.3° C.

| $^1$H-NMR data (CDCl$_3$, 400 MHz): δ = | 0.97 (t, 6H); |
| --- | --- |
| | 1.77 (m, 4H); |
| | 3.76 (s, 3H); |
| | 4.08 (t, 2H); |
| | 4.15 (m, 2H); |

Example 5

Preparation of Methyl N'-diphenoxymethylenehydrazinecarboxylate 4.31 g (46.9 mmol) of methyl carbazate were initially charged in water (40 ml) and admixed with 4.75 g (46.9 mmol) of conc. hydrochloric acid (36% strength). 10.0 g (46.9 mmol) of diphenyl imidocarbonate (preparation of diphenyl imidocarbonate similar to the method of Heydayatullah, M. *Bull Soc. Chim Fr.* 1967, 416) were added a little at a time to this solution, at 7° C. After 4 hours of stirring with ice-bath cooling, the mixture was extracted with ethyl acetate (4×100 ml). The combined organic phases were dried over magnesium sulphate and, after filtration, concentrated under reduced pressure. The residue was dried under reduced pressure at 25° C. This gave 7.62 g of crude product containing phenol and methyl N'-diphenoxymethylenehydrazinecarboxylate in a ratio of 10:1. The yield of methyl N'-diphenoxymethylenehydrazinecarboxylate was 693 mg (5%).

| $^1$H-NMR (DMSO-D$^6$, 400 MHz): δ = | 3.59 (s,3H); |
| --- | --- |
| | 7.21–7.50 (m, 10H); |
| | 9.05 (s, 1H). |

Example 6

Preparation of Methyl N'-(methoxymethylaminomethylene)hydrazinecarboxylate 0.95 g (5.00 mmol) of methyl N'-dimethoxymethylenehydrazinecarboxylate (85% pure) was admixed with 3.57 g of a 44% strength solution of methylamine (50 mmol) in methanol, and the mixture was stirred at room temperature for 3 days. Work-up and removal of the solvent gave 0.85 g (76%) of methyl N'-(methoxymethylaminomethylene)hydrazinecarboxylate in the form of an oil.

| $^1$H-NMR (DMSO-d$^6$, 400 MHz): δ = | 2.58 (d, 3H); |
| --- | --- |
| | 3.54 (s, 3H); |
| | 3.65 (s, 3H); |
| | 5.98 (s, 1H); |
| | 8.33 (s, 1H). |

Example 7

Preparation of 5-methoxy-4-methyl-2,4-dihydro-1,2,4-triazol-3-one 4.77 g (25.0 mmol) of methyl N'-dimethoxymethylenehydrazinecarboxylate (85% pure) were admixed with 15.3 g of a 51% strength solution of methylamine (250 mmol) in methanol, and the mixture was stirred at room temperature for 3 days. The orange-red solution was concentrated under reduced pressure to remove excess methylamine. This gave crude methyl N'-(methoxymethylaminomethylene)hydrazinecarboxylate which was then taken up in methanol (15 ml) and, with 4.95 g (27.5 mmol) of sodium methoxide solution (30% in methanol), heated to 50° C. After 3 h 50 min, the reaction mixture was cooled to room temperature, neutralized using 2N HCl and concentrated under reduced pressure. The residue was taken up in water (6 ml) and stored overnight in a fridge. The colourless crystals were filtered off, washed with cold water and dried under reduced pressure. This gave 1.70 g (52.7%) of 5-methoxy-4-methyl-2,4-dihydro-1,2,4-triazol-3-one in the form of a colourless solid. Melting point 146–148° C.

Example 8

Preparation of 5-methoxy-4-methyl-2,4-dihydro-1,2,4-triazol-3-one 8.11 g (0.05 mol) of methyl N'-dimethoxymethylenehydrazinecarboxylate were dissolved in 25.4 g of methanol and admixed with 3.26 g (0.105 mol) of methylamine, dissolved in methanol, and the mixture was heated in an autoclave at 70° C. for 14 hours. The reaction mixture was concentrated under reduced pressure and taken up in water (10 ml). The mixture was acidified by addition of conc. HCl. The crystals which precipitated at 4° C. were filtered off and dried. This gave 1.89 g (29.3%) of 5-methoxy-4-methyl-2,4-dihydro-1,2,4-triazol-3-one in the form of a colourless solid. Melting point 146–148° C.

| $^1$H-NMR (DMSO-d$^6$, 400 MHz): δ = | 2.96 (s, 3H); |
| --- | --- |
| | 3.90 (s, 3H); |
| | 10.88 (s, 1H). |

Preparation of 5-methoxy-4-methyl-2,4-dihydro-1,2,4-triazol-3-one 693.6 g (94.4%) of methyl N'-dipropoxymethylenehydrazinecarboxylate (3 mol) were dissolved in 1752 g of methanol and admixed with 564.7 g (6 mol) of methylamine, dissolved in ethanol, and the mixture was heated in an autoclave at 100° C. for 20 hours. The reaction mixture was concentrated under reduced pressure, the residue was taken up in water (880 ml) the mixture was extracted with methylene chloride and the extract was concentrated under reduced pressure. The crystals which precipitated out on cooling were filtered off and dried. This gave 383 g (71.2%, content 87.6%) of 5-propoxy-4-methyl-2,4-dihydro-1,2,4-triazol-3-one in the form of a solid. Melting point: 72.5–73.5° C.

| $^1$H-NMR data (DMSO-d$^6$, 400 MHz): δ = | 0.96 (t, 3H); |
| --- | --- |
| | 1.74 (m, 2H); |
| | 2.99 (s, 3H); |
| | 4.17 (t, 2H); |
| | 10.86 (s, NH). |

Example 10

Preparation of 5-propoxy-4-methyl-2,4-dihydro-1,2,4-triazol-3-one

In an autoclave, 10.02 g (44.3 mmol) of methyl N'-dipropoxymethylenehydrazinecarboxylate, 3.94 g of 39% strength solution of methylamine (49.9 mmol) in methanol and 46 g of methanol were initially charged. After 3 hours at 150° C., the solvent was distilled off. The crude substance was taken up in water (20 ml) and extracted repeatedly with methylene chloride. The organic solution was concentrated, giving 6.48 g of 5-propoxy-4-methyl-2,4-dihydro-1,2,4-triazol-3-one with a content of 50%, which corresponds to a yield of 46%.

Example 11

Preparation of 4-benzyl-5-propoxy-2,4-dihydro-1,2,4-triazol-3-one

In an autoclave, 2.04 g of methyl N'-dipropoxymethylenehydrazinecarboxylate (8.9 mmol) and 3.46 g of benzylamine (31.6 mmol) were initially charged in 25.8 g of methanol. After 5 hours at 110° C., the solvent was distilled off and the 4-methyl-5-propoxy-2,4-dihydro-1,2,4-triazol-3-one was recrystallized from ethyl acetate. This gave 0.57 g (27%) of pure 4-benzyl-5-propoxy-2,4-dihydro-1,2,4-triazol-3-one.

| $^1$H-NMR (DMSO-d$^6$, 400 MHz): δ = | 10.96 (s, 1H); |
| --- | --- |
| | 7.2–7.4 (m, 5H); |
| | 4.62 (s, 2H); |
| | 4.14 (t, 2H; J = 6.3 Hz); |
| | 1.66 (m, 2H); |
| | 0.84 (t, 3H; J = 7.4 Hz). |

| $^{13}$C-NMR (DMSO-D$^6$, 100 MHz): δ = | 153.2 (s); |
| --- | --- |
| | 151.0 (s); |
| | 136.5 (s); |
| | 128.5 (d, 2C); |
| | 127.5 (d); |
| | 127.2 (d, 2C); |
| | 70.2 (t); |
| | 42.3 (t); |
| | 21.4 (t); |
| | 9.9 (q). |

Example 12

Preparation of 4-cyclohexyl-5-propoxy-2,4-dihydro-1,2,4-triazol-3-one

In an autoclave, 2.04 g of methyl N'-dipropoxymethylenehydrazinecarboxylate (8.9 mmol) and 3.23 g of cyclohexylamine (32.2 mmol) were initially charged in 25.8 g of methanol. After 5 hours at 110° C., the solvent was distilled off and the crude 4-methyl-5-cyclohexyloxy-2,4-dihydro-1,2,4-triazol-3-one (1.3 g) was purified by column chromatography (mobile phase: ethyl acetate). This gave 0.37 g (18%) of pure product. Melting point: 132–136° C.

| $^1$H-NMR (DMSO-d$^6$, 400 MHz): δ = | 10.81 (s, 1H); |
| --- | --- |
| | 4.15 (t, 2H, J = 6.3 HZ); |
| | 1.77 (m, 2H); |
| | 0.96 (t, 3H, J = 7.4 Hz); |
| | 3.71 (m, 1H); |
| | 1.0–2.0 (m). |
| $^{13}$C-NMR (DMSO-D$^6$, 100 MHz): δ = | 152.8 (s); |
| | 151.2 (s); |
| | 70.1 (t); |
| | 51.0 (d); |
| | 29.9 (t, 2C); |
| | 25.2 (t, 2C); |
| | 24.7 (t); |
| | 21.5 (t); |
| | 10.1 (q). |

What is claimed is:

1. Process for preparing alkoxytriazolinones of the general formula

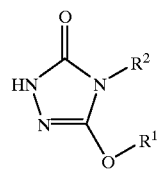

I in which $R^1$ and $R^2$ independently of one another are an optionally substituted alkyl group, aryl group, arylalkyl group or cycloalkyl group, characterized in that, in a first step, an iminocarbonic acid diester of the general formula

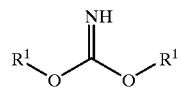

II in which $R^1$ has the abovementioned meaning, is reacted, in the presence of a mineral acid and dissolved in water or in a mixture of water with a water-miscible polar organic solvent, with a carbazinic acid ester of the general formula

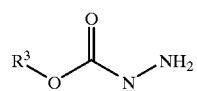

III in which $R^3$ is an optionally substituted alkyl group to give a hydrazinecarboxylic acid ester of the general formula

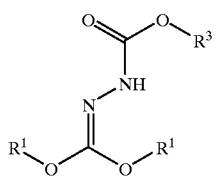

in which $R^1$ and $R^3$ have the meaning mentioned which is, in a second step, reacted in the presence of water, a polar organic solvent or mixtures thereof with an amine of the general formula $$R^2\text{—}NH_2 \qquad V$$

in which $R^2$ has the meaning mentioned, to give the end product of the formula I.

2. Process according to claim 1, characterized in that $R^1$ is a methyl, propyl or phenyl group.

3. Process according to claim 2, characterized in that $R^2$ is a methyl, benzyl or cyclohexyl group.

4. Process according to claim 3, characterized in that $R^3$ is a methyl group.

5. Process according to claim 4, characterized in that the mineral acid used in the first step is hydrochloric acid.

6. Process according to claim 5, characterized in that the reaction of the first step is carried out at a temperature from −5 to 40° C.

7. Process according to claim 6, characterized in that the polar organic solvent used in the second step is a straight-chain or branched alcohol having 1 to 6 C atoms.

8. Process according to claim 7, characterized in that the reaction of the second step is carried out at a temperature from 10 to 200° C.

9. Process according to claim 8, characterized in that the intermediate of the formula IV is isolated.

10. The process according to claim 1, wherein $R^2$ is a methyl, benzyl or cyclohexyl group.

11. The process according to claim 1, wherein $R^3$ is a methyl group.

12. The process according to claim 1, wherein the mineral acid used in the first step is hydrochloric acid.

13. The process according to claim 1, wherein the reaction of the first step is carried out at a temperature from −5° to 40° C.

14. The process according to claim 1, wherein the polar organic solvent used in the second step is a straight-chain or branched alcohol having 1 to 6 C atoms.

15. The process according to claim 1, wherein the reaction of the second step is carried out at a temperature from 100 to 200° C.

16. The process according to claim 1, wherein the intermediate of the formula IV is isolated.

* * * * *